United States Patent
Betzold et al.

(10) Patent No.: US 8,473,053 B2
(45) Date of Patent: *Jun. 25, 2013

(54) MINIMUM VENTRICULAR PACING TO BREAK THE REPETITIVE AR-VS PATTERN

(75) Inventors: Robert A. Betzold, Fridley, MN (US); Kevin E. Baumgart, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/212,359

(22) Filed: Aug. 18, 2011

(65) Prior Publication Data

US 2012/0221070 A1      Aug. 30, 2012

Related U.S. Application Data

(63) Continuation of application No. 12/604,578, filed on Oct. 23, 2009, now Pat. No. 8,024,042.

(51) Int. Cl.
*A61N 1/00* (2006.01)

(52) U.S. Cl.
USPC ............................................................ 607/9

(58) Field of Classification Search
USPC ............................................................ 607/9
See application file for complete search history.

(56) References Cited

U.S. PATENT DOCUMENTS 6,029,086 A * 2/2000 Kim et al. ......................... 607/9

* cited by examiner

*Primary Examiner* — George Manuel
(74) *Attorney, Agent, or Firm* — Reed A. Duthler; Stephen W. Bauer

(57) ABSTRACT

An implantable cardiac pacing device delivering minimum ventricular pacing and an associated method control intervals timed by the device during sensing and pacing. An atrial-only pacing mode is set in response to sensing intrinsic ventricular events in the ventricular chamber. A first post-ventricular atrial refractory period is set following each of a plurality of ventricular events sensed in the ventricular chamber, and atrial events each being sensed during first post-ventricular atrial refractory periods are detected. A second post-ventricular atrial refractory period is set in response to detecting the atrial events each being sensed during the first post-ventricular atrial refractory period.

18 Claims, 6 Drawing Sheets

MINIMUM VENTRICULAR PACING TO BREAK THE REPETITIVE AR-VS PATTERN

CROSS REFERENCE TO RELATED APPLICATION

This application is a continuation of U.S. patent application Ser. No. 12/604,578, filed Oct. 23, 2009, now U.S. Pat. No. 8,024,042, entitled "IMPROVEMENT TO MINIMUM VENTRICULAR PACING TO BREAK THE AR-VS PATTERN", incorporated herein by reference in it's entirety.

TECHNICAL FIELD

The disclosure relates generally to implantable medical devices and, in particular, to an implantable medical device and associated method for delivering minimum ventricular pacing.

BACKGROUND

Naturally conducted or intrinsic ventricular depolarizations have been recognized as being preferable over ventricular pacing in general and pacing in the right ventricular apex in particular. In order to minimize or greatly reduce ventricular pacing, protocols have been developed that, in general, utilize an atrial based timing mode that promotes intrinsic conduction whenever possible. Illustrative protocols are described, for example, in U.S. Pat. No. 7,218,965 (Casavant), U.S. Pat. No. 6,772,005 (Casavant), and U.S. Pat. No. 7,248,924 (Casavant), all of which are incorporated herein by reference in their entireties.

In general, during a minimum ventricular pacing (MVP) protocol, atrial-only pacing is delivered unless intrinsic ventricular events are not sensed. When a ventricular event is not sensed between two consecutive atrial events, a ventricular backup pacing pulse may be delivered after the second atrial event to avoid another cardiac cycle of asystole. When a specified number of atrial-only pacing cycles occur without sensing a ventricular event, the pacing device switches to a dual chamber pacing mode and delivers atrial and ventricular pacing pulses coordinated at a programmed atrial-ventricular (AV) delay.

Accurate sensing of intrinsic cardiac activity is important in maintaining the appropriate response of the pacing device and properly switching pacing mode without undue delay when changes in atrial-ventricular conductivity occur. When an atrial event is sensed, an atrial refractory period (ARP) is set. The atrial tissue cannot be depolarized again until after a physiological refractory period has expired and any earlier signals sensed by the pacing device during the atrial refractory period are likely to be far-field signals or other non-atrial events. As such, any "events" sensed during the ARP may be noted by the pacing device but are not used in resetting pacing escape interval timers used to control the timing and delivery of pacing pulses. When a ventricular event is sensed, a post-ventricular atrial refractory period (PVARP) is set. Any "events" sensed using atrial sensing electrodes during the PVARP may be noted but are also not used for resetting any escape interval timers used for controlling pacing intervals. The PVARP is useful in preventing far-field R-waves from being sensed as P-waves.

Premature ventricular contractions (PVCs) or undersensing of an atrial P-wave may cause two consecutive ventricular sense events with no intervening atrial sense event. In these situations a PVARP is set following the second ventricular sense event, which may be an extended PVARP. The next atrial event may occur during the PVARP resulting in a pattern of atrial refractory sense (AR) events followed by ventricular sensed (VS) events, i.e., an AR-VS pattern. This AR-VS pattern can become sustained as each subsequent ventricular sense event is followed by a PVARP, during which the next intrinsic atrial event occurs. The AR-VS pattern can cause a delay in the first back-up ventricular pacing pulse when AV conduction block returns and can cause user confusion when the AR-VS sensing pattern is observed. Pacing devices typically record counts of atrial and ventricular paced and sensed events to determine and report paced events as a percentage of the events counted. This reporting provides the clinician with a measure of the amount of pacing that is occurring. AR-VS event intervals may not be counted in such device diagnostics (since AR events are commonly ignored) resulting in the percentage of pacing being over-reported. A need remains, therefore, for improvements in MVP methods that avoid the aforementioned consequences of sustained AR-VS sensing patterns.

DETAILED DESCRIPTION

Figure 1:
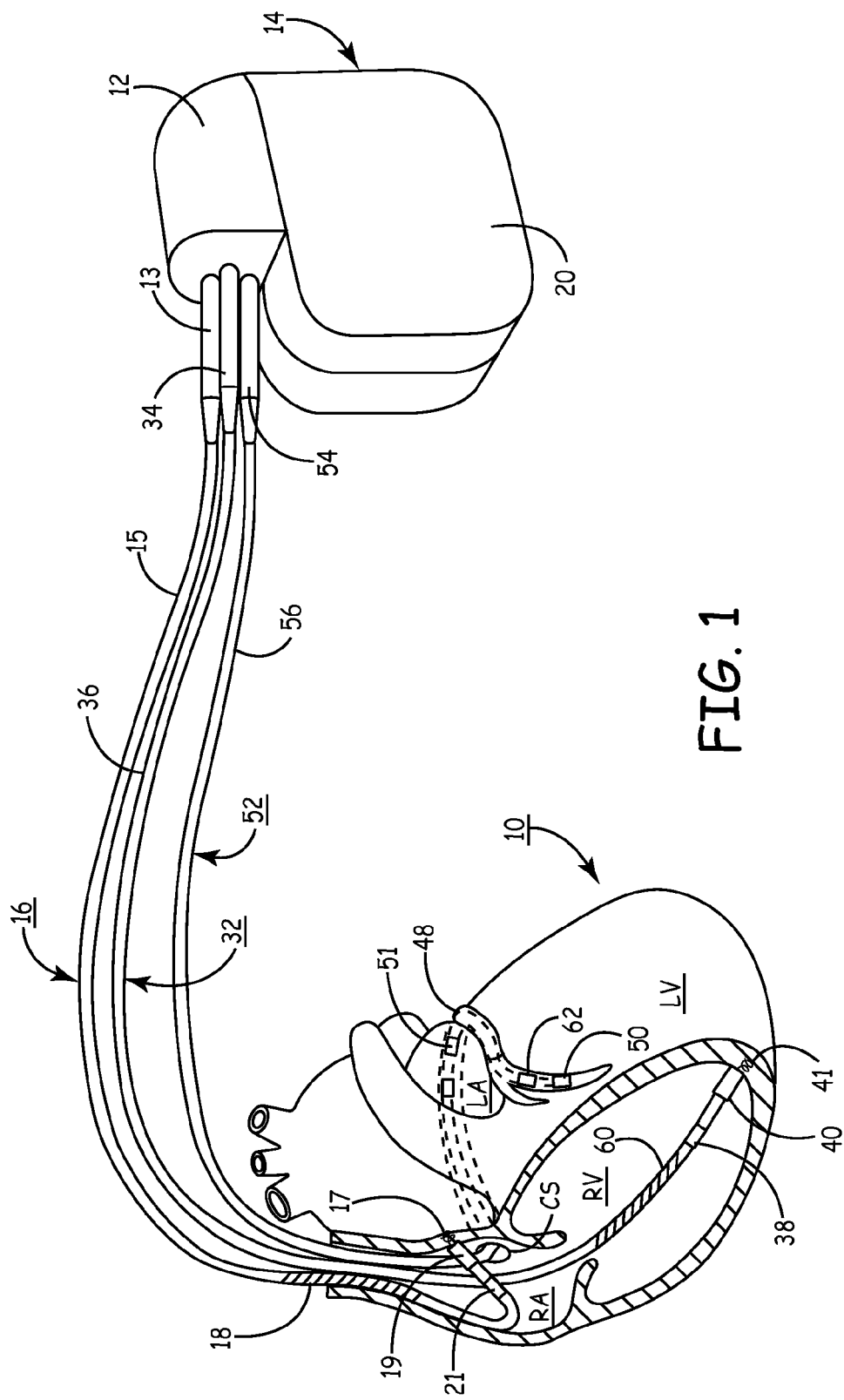
FIG. 1 depicts an implantable medical device (IMD) in which monitoring and pacing methods described herein may be implemented.

In the following description, references are made to illustrative embodiments. It is understood that other embodiments may be utilized without departing from the scope of the invention. In some instances, for purposes of clarity, identical reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

As used herein, an atrial based pacing mode is a mode that is programmed to pace in the atria, but only to sense in the ventricles. True single chamber atrial pacing would imply that only a single lead is present and ventricular activity may not be sensed in the ventricle nor would ventricular pacing be deliverable. In the present context an IMD operating in an atrial based mode includes at least ventricular sensing capabilities. Though not required, such a device would generally include ventricular pacing as well. However, in order to deliver ventricular pacing the device would switch pacing modes from the atrial only pacing mode to a dual chamber pacing mode, such as DDD.

FIG. 1 depicts an implantable medical device (IMD) 14 in which monitoring and pacing methods described herein may be implemented. Various embodiments of the invention may be implemented in numerous types of implantable medical devices capable of sensing cardiac signals, such as pacemakers, ECG monitors, and hemodynamic monitors. IMD 14 is provided for sensing intrinsic heart activity and delivering cardiac stimulation pulses in the form of pacing, cardioversion or defibrillation therapy, as appropriate, to one or more heart chambers.

IMD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 connect IMD 14 with the RA, the RV and the LV, respectively. Each lead has at least one electrical conductor and pace/sense electrode. A remote indifferent can electrode is formed as part of the outer surface of the IMD housing 20. The pace/sense electrodes and the remote indifferent can electrode can be selectively employed to provide a number of unipolar and bipolar pace/sense electrode combinations for pacing and sensing functions.

RA lead 16 is passed through a vein into the RA chamber and may be attached at its distal end to the RA wall using an optional fixation member 17. RA lead 16 is formed with a connector 13 fitting into a connector bore of IMD connector block 12 for electrically coupling RA tip electrode 19 and RA ring electrode 21 to IMD circuitry housed within housing 20 via insulated conductors extending within lead body 15. RA tip electrode 19 and RA ring electrode 21 may be used in a bipolar fashion, or in a unipolar fashion with IMD housing 20, for achieving RA stimulation and sensing of RA EGM signals. RA lead 16 is optionally provided with a coil electrode 18 that may be used for delivering high voltage cardioversion/defibrillation pulses to heart 10 in response to the detection of tachycardia or fibrillation.

RV lead 32 is passed through the RA into the RV where its distal end, carrying RV tip electrode 40 and RV ring electrode 38 provided for stimulation in the RV and sensing of RV EGM signals, is fixed in place in the RV apex by a distal fixation member 41. RV lead 32 optionally carries a high-voltage coil electrode 60 for use in cardioverting and defibrillating heart 10. RV lead 32 is formed with a connector 34 fitting into a corresponding connector bore of IMD connector block 12. Connector 34 is coupled to electrically insulated conductors within lead body 36 and connected with distal tip electrode 40, ring electrode 38 and coil electrode 60.

Coronary sinus lead 52 is passed through the RA, into the CS and further into a cardiac vein 48 to extend the distal LV tip electrode 50 and ring electrode 62 alongside the LV chamber to achieve LV stimulation and sensing of LV EGM signals. The LV CS lead 52 is coupled at the proximal end connector 54 into a bore of IMD connector block 12 to provide electrical coupling of conductors extending from electrodes 50 and 62 within lead body 56 to IMD internal circuitry. In some embodiments, LV CS lead 52 could bear a proximal LA pace/sense electrode 51 positioned along CS lead body 56 such that it is disposed proximate the LA for use in stimulating the LA and/or sensing LA EGM signals.

In addition to the lead-mounted electrodes, IMD 14 may include one or more subcutaneous cardiac sensing electrodes (not shown) formed as uninsulated portions of the IMD housing 20 or included in the connector block 12. While a particular IMD system with associated leads and electrodes is illustrated in FIG. 1, numerous implantable cardiac monitoring, pacemaker and IMD system configurations are possible, which may include one or more leads deployed in transvenous, subcutaneous, or epicardial locations. The lead and electrode arrangements will depend on the particular application. Methods described herein may also be implemented in a subcutaneous cardiac monitor, pacemaker or IMD system in which electrodes are formed as a part of the device housing and/or carried by subcutaneous leads.

IMD 14 is shown as a multi-chamber device capable of sensing and stimulation in three or all four heart chambers. It is understood that IMD 14 may be modified to operate as a dual chamber device or a single chamber device having dual chamber sensing capabilities. The illustrative embodiments described herein generally relate to a pacemaker or IMD having at least dual chamber (atrial and ventricular) pacing and sensing capabilities. It is contemplated that the methods described, however, may be adapted for use in a single chamber device by using far-field sensing of ventricular events or using a hemodynamic signal for identifying the timing of ventricular mechanical events. Pacing devices configured to operate in a MVP mode of operation are typically provided as dual chamber pacemakers.

Figure 2:
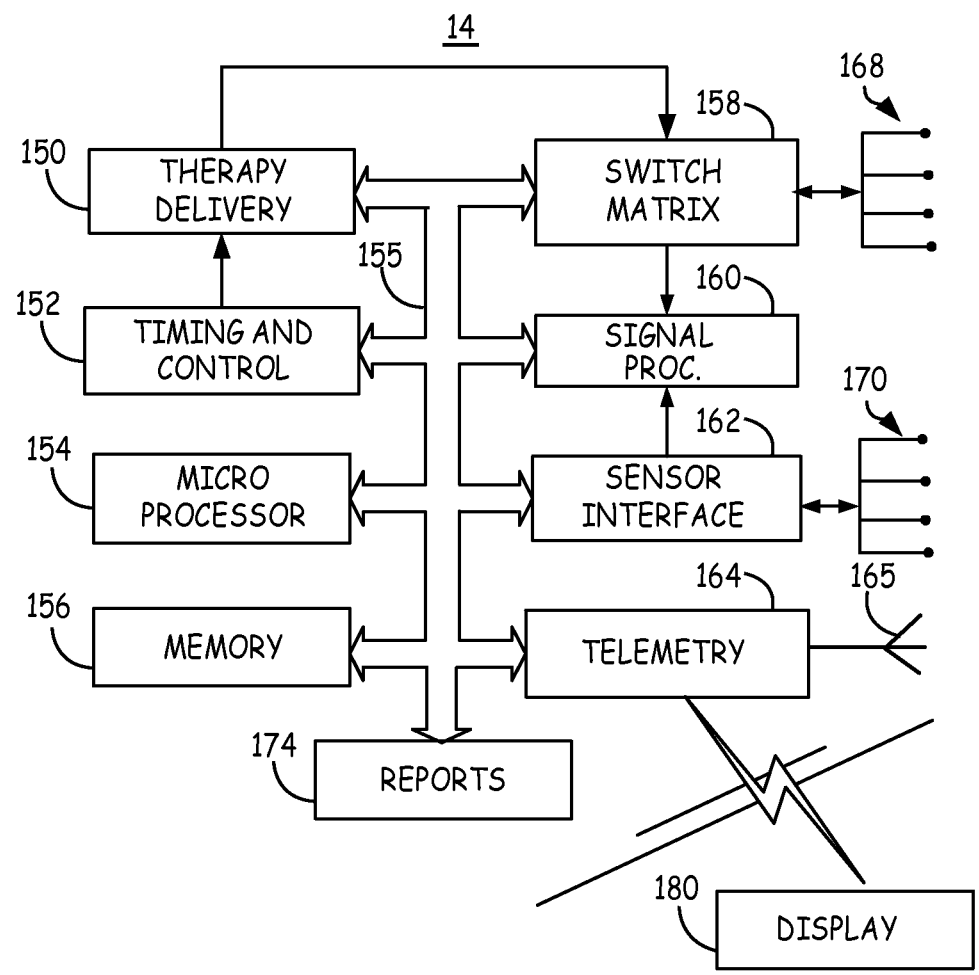
FIG. 2 is a functional block diagram of the IMD shown in FIG. 1 according to one embodiment.

FIG. 2 is a functional block diagram of the IMD 14 shown in FIG. 1 according to one embodiment. IMD 14 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 14 via a data/address bus 155. IMD 14 includes therapy delivery module 150 for delivering electrical stimulation therapies, such as cardiac pacing therapies and arrhythmia therapies including cardioversion/defibrillation shocks and anti-tachycardia pacing (ATP), under the control of timing and control 152. Therapy delivery module 150 is typically coupled to two or more electrodes 168 via an optional switch matrix 158. Electrodes 168 may correspond to any of the electrodes shown in FIG. 1. Switch matrix 158 may be used for selecting which electrodes and corresponding polarities are used for delivering electrical stimulation pulses.

Cardiac electrical signals are sensed for use in determining when an electrical stimulation therapy is needed and in controlling a stimulation mode and the timing of stimulation pulses. Electrodes 168 used for sensing are coupled to signal processing circuitry 160. Signal processor 160 includes sense amplifiers and may include other signal conditioning circuitry and an analog-to-digital converter. Electrical signals may then be used by microprocessor 154 or other control circuitry for detecting physiological events, such as detecting and discriminating cardiac arrhythmias or detecting the need for pacing. Signal processing circuitry 160 may include event detection circuitry generally corresponding to P-wave detection and R-wave detection circuitry.

IMD 14 may optionally be coupled to one or more physiological sensors 170, shown schematically. Physiological sensors 170 may include a pressure sensor, a motion sensor or accelerometer, a flow sensor, blood chemistry sensors such as an oxygen saturation sensor, activity sensors, an acoustical sensor, or other physiological sensors. Physiological sensors may be carried by any lead extending from IMD 14, incorporated in or on the IMD housing or may be embodied as leadless sensors implanted in the body and in telemetric communication with the IMD or another device. Signals from sensors 170 are received by a sensor interface 162 which provides sensor signals to signal processing circuitry 160. Sensor signals are used by microprocessor 154 for detecting physiological events or conditions.

In various embodiments, IMD 14 includes rate responsive pacing in which an activity sensor, oxygen sensor, respiration sensor, or other sensor generating a signal correlated to changes in metabolic demand, referred to generally as "demand sensor", or any combination of demand sensors, is used to compute a sensor-indicated rate (SIR). Timing and control module 152 responds to the SIR by adjusting an atrial pacing rate up or down between a programmed lower rate and a maximum upper rate.

The IMD operating system includes associated memory 156 for storing a variety of operating algorithms and parameter values that are used by microprocessor 154. Algorithms and control parameters used for controlling minimum ventricular pacing, delivering rate responsive pacing, detecting arrhythmias, delivering arrhythmia therapy, monitoring event intervals, and monitoring autonomic function may be stored in memory 156. The memory 156 may also be used for storing data compiled from sensed EGM signals and/or relating to device operating history for telemetry out on receipt of a retrieval or interrogation instruction.

IMD 14 further includes telemetry circuitry 164 and antenna 165. Programming commands or data are transmitted during uplink or downlink telemetry between IMD telemetry circuitry 164 and external telemetry circuitry included in a programmer or monitoring unit. Report module 174 may compile data acquired by the IMD 14 for transmitting via telemetry circuitry 164 to an external display 180, which may be implemented in a programmer, personal computer, web-based or local network, or other communication device in communication with IMD 14. In one embodiment, data relating to a percentage of time pacing in the atria and/or ventricles and other heart rhythm information is compiled in a medical report that is transmitted to display 180 to be presented in a text or graphical display to a clinician.

Figure 3:
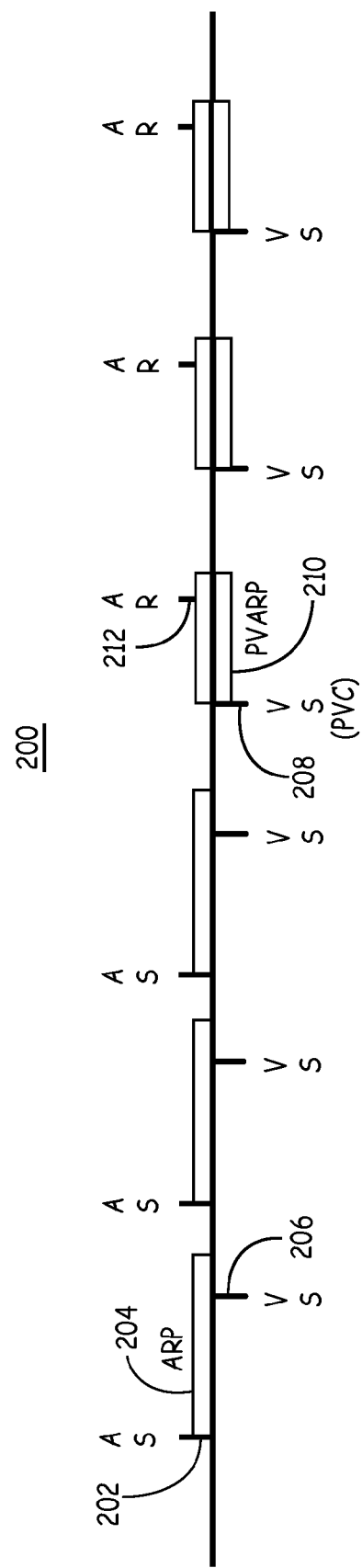
FIG. 3 is a timeline depicting sensed atrial and ventricular events.

FIG. 3 is a timeline 200 depicting atrial and ventricular events sensed by a pacing device. The pacing device is sensing in both an atrium (events depicted on the upper portion of the time line 200) and a ventricle (events depicted on the lower portion of time line 200). The pacing device is operating in a MVP mode in which atrial-only pacing is in effect during intact atrial-ventricular conduction, as evidenced by the intrinsic ventricular sensed (VS) events 206. Intrinsic atrial sensed (AS) events 202 are occurring at a rate faster than a programmed atrial pacing rate, causing atrial pacing pulses to be withheld. In other words, an atrial pace escape interval timer restarted upon each AS event 202 does not expire before the next AS event. An ARP 204 is started upon each AS event 202 such that any atrial events sensed during the ARP 204 are ignored for purposes of setting pacing timing intervals.

A VS event 208 is seen to occur following a previous VS event without an intervening AS event. The VS event 208 may be a premature ventricular contraction (PVC) as indicated in the example of FIG. 3. In other cases, two consecutive VS events may occur without an intervening AS event when an atrial P-wave is undersensed. Subsequent to the VS event 208, a PVARP 210 is started. The next atrial event that is sensed occurs during PVARP 210 resulting in an atrial refractory (AR) event 212. The AR event 212 is ignored by the pacing device for the purposes of starting pacing timing intervals. The next VS event occurs without a preceding AS event and marks the start of another PVARP interval. As a result, the next atrial event is again an AR event. This AR-VS pattern, which can be conversely referred to as a VS-AR pattern, may be sustained indefinitely until a change in the heart rhythm occurs that results in either an atrial event outside PVARP 210, a missed or undersensed ventricular event that prevents PVARP 210 from being set, or a mode switch to dual chamber pacing occurs due to a lack of intrinsic ventricular events.

Figure 4:
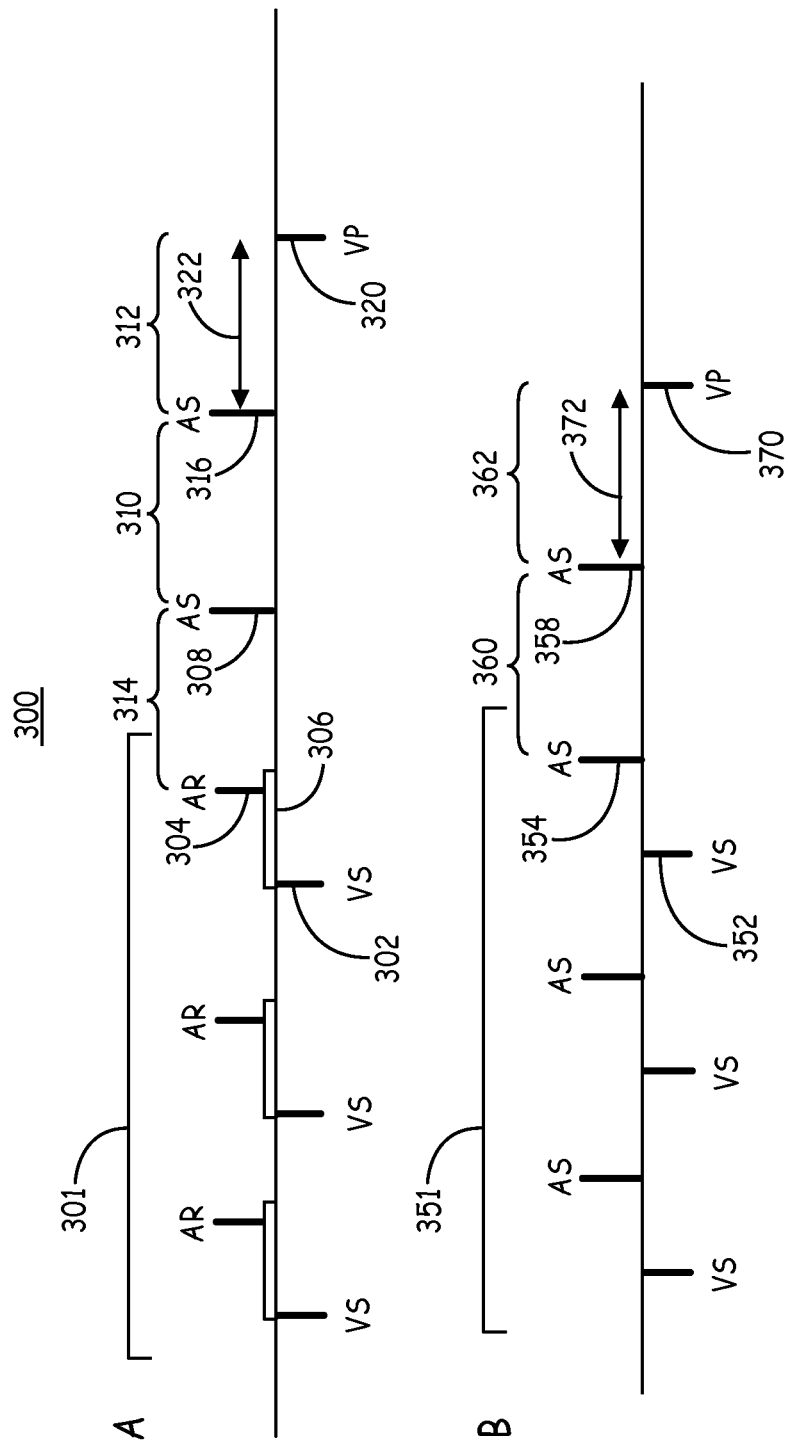
FIG. 4 is an EGM recording illustrating the delivery of a back-up ventricular pacing pulse during an atrial based pacing mode during MVP.

FIG. 4 is an EGM recording 300 illustrating the delivery of a back-up ventricular pacing pulse during atrial-only pacing.

In panel A, a sustained pattern of AR-VS sensing 301 is shown. The pacing device is operating in an atrial-only pacing mode during MVP. Transient atrial-ventricular conduction block may occur resulting in ventricular asystole beginning on cardiac cycle 314. The last AR event 304 is not used by the pacing device in setting pacing intervals. As such, the AR-AS cycle 314 is not used to start a ventricular pace time interval. The next atrial event 308 is sensed outside of PVARP 306 since no ventricular event occurred after AR event 304 to cause a PVARP to be reset. No ventricular event is sensed during the first AS-AS cycle 310. A ventricular back-up pacing interval 322 is therefore set upon sensing the AS event 316 that is not preceded by a ventricular sensed event during AS-AS cycle 310. Upon the expiration of the ventricular pace interval 322, a backup ventricular pace (VP) 320 is delivered. The AR-AS interval 314 that occurs as a result of the sustained AR-VS sensing pattern effectively delays the delivery of a backup VP by one cardiac cycle.

In comparison, as shown in panel B, when intrinsic atrial and ventricular events are properly sensed in an AS-VS pattern 351, the last VS event 352 is followed by an AS event 354. When the next AS event 358 occurs resulting in an AS-AS interval 360 without an intervening VS event, the backup VP timing interval 372 is started. AVP 370 is delivered upon expiration of timing interval 372 such that only a single asystolic cardiac cycle 360 occurs. The VP 370 occurs earlier, approximately one cardiac cycle earlier, during accurate AS-VS sensing 351, as compared to the result during an AR-VS sensing pattern 301 as shown in Panel A. Thus, it is desirable to interrupt a sustained AR-VS sensing pattern and restore a proper AS-VS pattern to promote a prompt and appropriate response by the pacing device to changes in heart rhythm.

Figure 5:
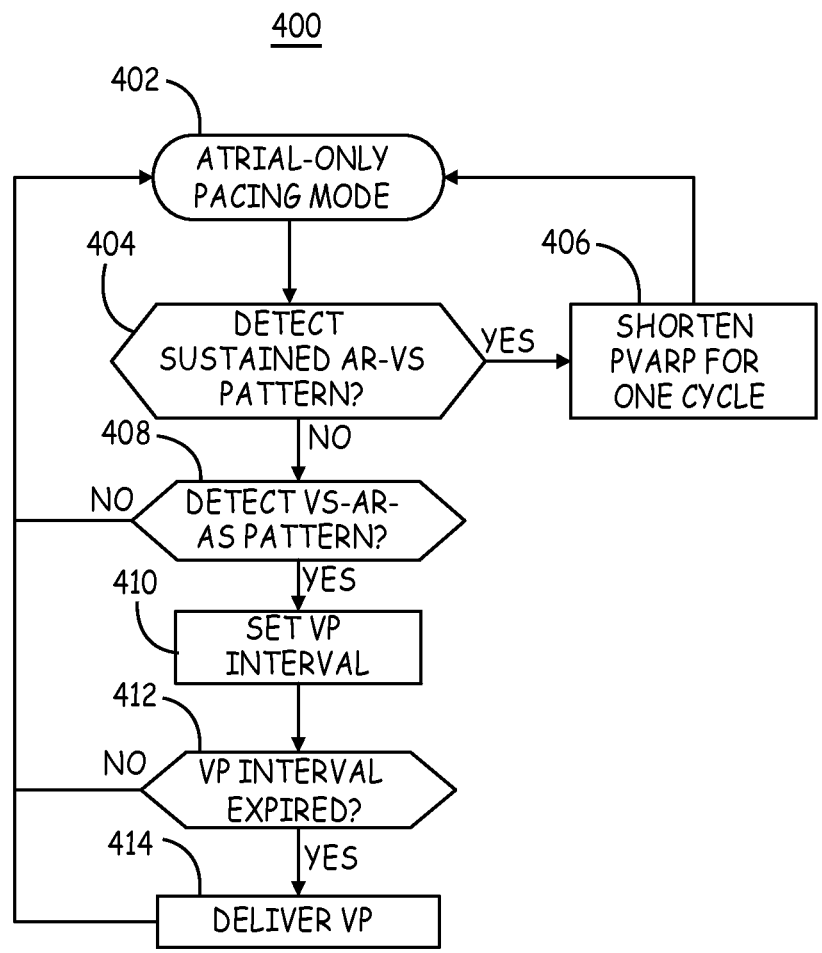
FIG. 5 is a flow chart of a method for terminating an AR-VS sensing pattern during MVP.

FIG. 5 is a flow chart 400 of a method for terminating an AR-VS sensing pattern during MVP. Flow chart 400 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The process shown in the flow chart 400 is performed when the pacing device is operating in an atrial-only pacing mode during MVP as indicated at block 402. At block 404, atrial and ventricular sensed events are analyzed to determine if a sustained AR-VS pattern is detected. A sustained AR-VS pattern may be detected when a specified number of consecutive AR events are detected. In one embodiment, the AR events are counted and if the counter reaches a specified number, e.g. eight AR events, a sustained AR-VS pattern is detected. An AS event would reset the counter. The counts used to detect sustained atrial refractory sensing may include counts of consecutive AR events, AR-VS sequences, or VS-AR sequences.

Upon detecting the sustained AR-VS pattern, the PVARP set in response to the next VS event is set at block 406 to an interval shorter than an initial PVARP being set during the sustained AR-VS sensing pattern. The shortened PVARP may be a predetermined interval less than the initial PVARP or may even be set to 0 ms.

Figure 6:
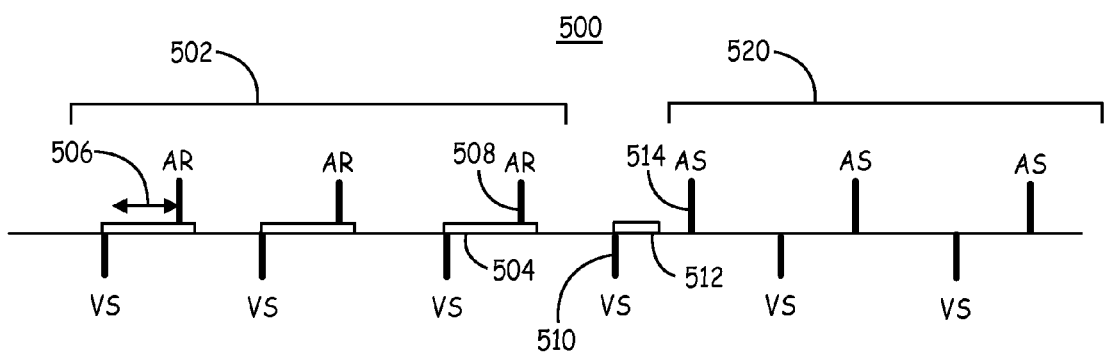
FIG. 6 is a time line of a sustained AR-VS pattern terminated by setting a single, shortened PVARP.

FIG. 6 is a time line 500 of a sustained AR-VS pattern 502 terminated by setting a single, shortened PVARP 512. A sustained AR-VS pattern 502 is detected upon sensing the nth consecutive AR event 508, where n is a previously specified number of consecutive AR events defined as criteria for detecting a sustained AR-VS sensing pattern. In response to detecting the sustained AR-VS pattern, the PVARP 512 is set following the nth VS event 510 to a shortened interval relative to the PVARP 504 applied during the AR-VS pattern 502. The shortened PVARP 512 will cause the next atrial event 514 to be a non-refractory event sensed outside the PVARP thereby terminating the AR-VS pattern and establishing an AS-VS sensing pattern 520. The AS-VS pattern 520 is established and the atrial-only pacing mode of the pacing device is maintained.

The shortened PVARP 512 may be set to a previously specified interval or a specified decrement less than the initial PVARP 504. In some embodiments, a VS-AR interval 506 is measured during the sustained AR-VS pattern 502. The shortened PVARP 512 is set to be shorter than the measured VS-AR interval 506 to promote sensing of the next atrial event 514 outside the shortened PVARP 512. For example, the shortened PVARP 512 may be set to approximately 50 ms, or a larger decrement, less than the measured VS-AR interval 506. The VS-AR interval measurement used to set the shortened PVARP 512 may be a single interval measurement or a minimum, average or other measure of multiple VS-AR intervals.

Referring again to flow chart 400 in FIG. 5, the process may optionally monitor for a VS-AR-AS pattern at block 408 during atrial-only pacing. If a VS-AR-AS pattern occurs, the AR-AS cycle may represent a cycle of ventricular asystole. In this case, the backup ventricular pace interval may be started at block 410 upon sensing the AS event of a VS-AR-AS pattern so that delivery of a ventricular backup pace is not delayed by the AR event. In other words, the AR-AS sequence occurring without an intervening VS event is used in setting a VP timing interval rather than waiting for an AS-AS interval. Additional criteria may be applied at block 410 for detecting a VS-AR-AS pattern that may be associated with ventricular asystole. For example, a preceding AR event may be required such that the pattern AR-VS-AR-AS is detected at block 408. Other requirements may include a PVC detected prior to the VS-AR-AS pattern, i.e. a VS-VS cycle detected without an intervening atrial event. The VS-VS cycle may be the immediately preceding cycle leading into the VS-AR-AS pattern (i.e., VS-VS-AR-AS) or a VS-VS cycle may be required to have occurred within a preceding number of cardiac cycles prior to the VS-AR-AS pattern with all intervening atrial events being AR events. Such a pattern can be represented by VS-VS-AR-(VS-AR)$_i$-AS where i may be any number that is less than the specified number of consecutive AR events required to detect a sustained AR-VS pattern. Evidence of a previous VS-VS cycle or a preceding AR-VS interval leading up to the detected VS-AR-AS pattern suggests that the atrial refractory event occurring in the VS-AR-AS pattern may actually be a normal atrial depolarization and may be appropriately used in setting a backup VP timing interval.

If the backup VP interval expires as determined at block 412, a ventricular pacing pulse is delivered at block 414 and the process returns to block 402. The pacing device remains in the atrial-only pacing mode. If the VP interval does not time out, i.e. a VS event is sensed prior to expiration of the VP interval, the process returns to block 402 without delivering the ventricular pacing pulse.

Thus, a pacing device and associated method have been presented in the foregoing description with reference to specific embodiments. It is appreciated that various modifications to the referenced embodiments may be made without departing from the scope of the invention as set forth in the following claims.

The invention claimed is:

1. A method for controlling intervals timed by an implantable cardiac pacing device configured for delivering cardiac pacing, the method comprising:
   sensing intrinsic atrial events in an atrial chamber;
   sensing intrinsic ventricular events in a ventricular chamber;
   setting a first post-ventricular atrial refractory period following each of a plurality of ventricular events sensed in the ventricular chamber;
   detecting a plurality of atrial events each being sensed during first post-ventricular atrial refractory periods; and
   setting a second post-ventricular atrial refractory period following a single intrinsic ventricular event in response to detecting the plurality of atrial events, the second post-ventricular atrial refractory period being shorter than the first post-ventricular atrial refractory period so that a next intrinsic atrial event is sensed outside the second post-ventricular atrial refractory period and establishes a pattern of an atrial non-refractory event sensed in the atrial chamber (AS) followed by a ventricular event sensed in the ventricular chamber (VS).

2. The method of claim 1 wherein setting the second post-ventricular atrial refractory period comprises:
   measuring an interval between a sensed ventricular event and an atrial event sensed during the first post-ventricular atrial refractory period; and
   setting the second post-ventricular atrial refractory period to be less than the measured interval.

3. The method of claim 1 wherein the second post-ventricular atrial refractory period is set to zero ms.

4. The method of claim 1 wherein detecting the plurality of atrial events comprises detecting a predetermined number of consecutive atrial events each sensed during consecutive first post-ventricular atrial refractory periods.

5. The method of claim 1 further comprising:
   detecting a VS-AR-AS pattern upon sensing an atrial event within the first post ventricular atrial refractory period and sensing a subsequent intrinsic atrial event outside a first post ventricular atrial refractory period without sensing an intervening ventricular event;
   setting a ventricular pacing escape interval in response to detecting the VS-AR-AS pattern; and
   delivering a ventricular pace upon expiration of the pacing escape interval.

6. The method of claim 5 further comprising sensing at least one atrial event during a first post ventricular atrial refractory period preceding the detected VS-AR-AS pattern prior to setting the ventricular pacing escape interval.

7. An implantable medical device configured to control timing intervals used by the device for sensing cardiac activity and delivering cardiac pacing pulses, the device comprising:
   an atrial pacing and sensing lead for delivering atrial pacing pulses and sensing atrial signals;

a ventricular pacing and sensing lead for delivering ventricular pacing pulses and sensing ventricular signals;

a sensing module coupled to the atrial and ventricular pacing and sensing leads, the sensing module responsive to intrinsic depolarization events of a heart;

a pulse generator producing cardiac stimulation pulses delivered via the atrial and ventricular pacing and sensing leads; and a control module coupled to the sensing module and the therapy delivery module, the control module configured to:

set a first post-ventricular atrial refractory period following each of a plurality of ventricular events sensed in the ventricular chamber;

detect a plurality of atrial events each being sensed during first post-ventricular atrial refractory periods;

set a second post-ventricular atrial refractory period following a single sensed ventricular event in response to detecting the plurality of atrial events, the second post-ventricular atrial refractory period being shorter than the first post-ventricular atrial refractory period so that a next intrinsic atrial event is sensed outside the second post-ventricular atrial refractory period and establishes a pattern of an atrial non-refractory event sensed in the atrial chamber (AS) followed by a ventricular event sensed in the ventricular chamber (VS).

8. The device of claim 7 wherein the control module is further configured to:

measure an interval between a sensed ventricular event and an atrial event sensed during the first post-ventricular atrial refractory period; and set the second post-ventricular atrial refractory period to be less than the measured interval.

9. The device of claim 7 wherein the control module is configured to set the second post-ventricular atrial refractory period is set to zero ms.

10. The device of claim 7 wherein the control module is configured to detect the plurality of atrial events by detecting predetermined number of consecutive atrial events each sensed during consecutive first post-ventricular atrial refractory periods.

11. The device of claim 7 wherein the control module is further configured to:

detect a VS-AR-AS pattern upon sensing an atrial event within the first post ventricular atrial refractory period and sensing a subsequent intrinsic atrial event outside a first post ventricular atrial refractory period without sensing an intervening ventricular event;

set a ventricular pacing escape interval in response to the VS-AR-AS pattern; and deliver a ventricular pacing pulse upon expiration of the pacing escape interval.

12. The device of claim 11 wherein the control module is further configured to sense at least one atrial event during a first post ventricular atrial refractory period preceding the detected VS-AR-AS pattern prior to setting the ventricular pacing escape interval.

13. A computer-readable medium storing a set of instructions which when implemented in an implantable medical device configured to control timing intervals used by the device for sensing cardiac activity and deliver cardiac pacing pulses and cause the device to:

sense intrinsic atrial events in an atrial chamber;

sense intrinsic ventricular events in a ventricular chamber;

set a first post-ventricular atrial refractory period following each of a plurality of ventricular events sensed in the ventricular chamber;

detect a plurality of atrial events each being sensed during first post-ventricular atrial refractory periods; and set a second post-ventricular atrial refractory period following a single intrinsic ventricular event in response to detecting the plurality of atrial events, the second post-ventricular atrial refractory period being shorter than the first post-ventricular atrial refractory period so that a next intrinsic atrial event is sensed outside the second post-ventricular atrial refractory period and establishes a pattern of an atrial non-refractory event sensed in the atrial chamber (AS) followed by a ventricular event sensed in the ventricular chamber (VS).

14. The computer-readable medium of claim 13 further comprising instructions which cause the device to:

measure an interval between a sensed ventricular event and an atrial event sensed during the first post-ventricular atrial refractory period; and set the second post-ventricular atrial refractory period to be less than the measured interval.

15. The computer-readable medium of claim 13 further comprising instructions which cause the device to set the second post-ventricular atrial refractory period is set to zero ms.

16. The computer-readable medium of claim 13 further comprising instructions which cause the device to detect the plurality of atrial events by detecting predetermined number of consecutive atrial events each sensed during consecutive first post-ventricular atrial refractory periods.

17. The computer-readable medium of claim 13 further comprising instructions which cause the device to:

detect a VS-AR-AS pattern upon sensing an atrial event within the first post ventricular atrial refractory period and sensing a subsequent intrinsic atrial event outside a first post ventricular atrial refractory period without sensing an intervening ventricular event;

set a ventricular pacing escape interval in response to the VS-AR-AS pattern; and deliver a ventricular pacing pulse upon expiration of the pacing escape interval.

18. The computer-readable medium of claim 17 further comprising instructions which cause the device to sense at least one atrial event during a first post ventricular atrial refractory period preceding the detected VS-AR-AS pattern prior to setting the ventricular pacing escape interval.

* * * * *